United States Patent [19]

Larson et al.

[11] Patent Number: 5,802,134
[45] Date of Patent: Sep. 1, 1998

[54] NUTATING SLICE CT IMAGE RECONSTRUCTION APPARATUS AND METHOD

[75] Inventors: Gregory L. Larson, Newton; Christopher C. Ruth, Danvers; Carl R. Crawford, Brookline, all of Mass.

[73] Assignee: Analogic Corporation, Peabody, Mass.

[21] Appl. No.: 831,558

[22] Filed: Apr. 9, 1997

[51] Int. Cl.$^6$ ...................................................... A61B 6/03
[52] U.S. Cl. ........................... 378/4; 378/15; 378/901
[58] Field of Search ............................ 378/4, 15, 901; 250/363.02, 363.04, 363.1, 370.08, 370.09, 370.1

[56] References Cited

U.S. PATENT DOCUMENTS

| | | | |
|---|---|---|---|
| 5,396,528 | 3/1995 | Hu et al. | 378/14 |
| 5,469,486 | 11/1995 | Hu et al. | 378/4 |
| 5,485,493 | 1/1996 | Heuscher et al. | 378/15 |

OTHER PUBLICATIONS

Yan, et al., "Cone beam tomography with circular, elliptical and spiral orbits," Phys. Med. Biol., 1992, vol. 37, No. 3, pp. 493–506.

Wang, et al., "A General Cone–Beam Reconstruction Algorithm," IEEE Transactions on Medical Imaging, vol. 12., No. 3, Sep. 1993, pp. 486–496.

Defrise, et al., "A Cone–Beam Reconstruction Algorithm Using Shift Variant Filtering and Cone–Beam Backprojection," IEEE Transactions on Medical Imaging, vol. 13, No. 1, Mar. 1994, pp. 186–195.

Crawford, et al., "Computed tomography scanning with simultaneous patient translation," Med. Phys. 17 (6), Nov./Dec. 1990, pp. 967–982.

Feldkamp, et al., "Practical cone–beam algorithm," Optical Society of America, vol. 1, No. 6, Jun. 1984, pp. 612–619.

Kudo, et al., "Helical–Scan Computed Tomography Using Cone–Beam Projections," Journal of Electronics, Information and Communication Society J74–D–II, 1991.

*Primary Examiner*—David P. Porta
*Assistant Examiner*—David Vernon Bruce
*Attorney, Agent, or Firm*—Lappin & Kusmer

[57] ABSTRACT

A nutating slice CT image reconstruction apparatus and method generates a set of projection data using helical cone-beam scanning. The three-dimensional projection data is used to reconstruct a series of planar image slices. The slices are selected such that they define a tilt angle and a rotation angle with respect to the longitudinal axes of the object being scanned. Successive slices have equal tilt angles but changing rotation angles such that normal axes of successive slices define a nutation and precession about the longitudinal axis of the object. Projection data for the tilted slices are formed of selected one-dimensional fan-beam data. As such, the projection data can be applied to conventional two-dimensional reconstruction approaches to generate an image.

49 Claims, 10 Drawing Sheets

NUTATING SLICE CT IMAGE RECONSTRUCTION APPARATUS AND METHOD

FIELD OF THE INVENTION

The present invention relates generally to computed tomography (CT) imaging and more particularly to three-dimensional CT imaging with improved efficiency and reduced image artifacts.

BACKGROUND OF THE INVENTION

FIG. 1 is a schematic axial view of a typical conventional CT scanner 10 which includes an x-ray source 12 and an x-ray detector system 14 secured to diametrically opposite sides of an annular shaped disk 16. The disk 16 is rotatably mounted within a gantry support (not shown), so that during a scan the disk 16 continuously rotates about a z-axis while x-rays pass from the source 12 through an object, such as a patient 20 positioned on a patient table 56 within the opening of the disk 16. The z-axis is normal to the plane of the page in FIG. 1 and intersects the scanning plane at the mechanical center of rotation 18 of the disk 16. The mechanical center of rotation 18 of the disk corresponds to the "isocenter" of the reconstructed image.

In one conventional system, the detector system 14 includes an array of individual detectors 22 disposed in a single row in a shape of an arc having a center of curvature at the point 24, referred to as the "focal spot," where the radiation emanates from the x-ray source 12. The source 12 and array of detectors 22 are positioned so that the x-ray paths between the source and each detector all lie in a "scanning plane" that is normal to the z-axis. Since the x-ray paths originate from what is substantially a point source and extend at different angles to the detectors, the x-ray paths form a "fan beam" 26 that is incident on the detector array 14 in the form of one-dimensional linear projection. The x-rays incident on a single detector at a measuring instant during a scan are commonly referred to as a "ray," and each detector generates an output signal indicative of the intensity of its corresponding ray. Since each ray is partially attenuated by all the mass in its path, the output signal generated by each detector is representative of the attenuation of all the mass disposed between that detector and the x-ray source, i.e., the attenuation of the mass lying in the detector's corresponding ray path.

The output signals generated by the x-ray detectors are normally processed by a signal processing portion (not shown) of the CT system. The signal processing portion generally includes a data acquisition system (DAS), which filters the output signals generated by the x-ray detectors to improve their signal-to-noise ratio (SNR). The output signals generated by the DAS during a measuring interval are commonly referred to as a "projection" or "view" and the angular orientation of the disk 16, source 12 and detector system 14 corresponding to a particular projection is referred to as the "projection angle."

FIG. 2 illustrates the orientation of the disk 16, x-ray source 12 and detector system 14 for generation of a fan beam data point $P_f(\beta, \gamma)$ at a projection angle $\beta$ and a detector angle $\gamma$. A center line 40, which is used to define reference orientations, extends from the focal spot of the x-ray source 12 through the z-axis at the mechanical center of rotation 18. The projection angle $\beta$ is defined as the angle between a vertical axis and the center line 40. Each individual detector in system 14 has an associated detector angle $\gamma$ that is also defined with respect to the center line 40. By definition, the center line 40 intersects the detector system 14 at a reference detector angle $\gamma$ of 0°.

A symmetric detector system 14 as shown in FIG. 2 extends from a detector angle of $-\delta$ to $+\delta$, where $\delta$ is one-half the fan angle. A fan beam view or projection $P_f(\beta, \gamma)$ generated by symmetric detector system 14 includes a set of data points $P_f(\beta, \gamma)$, generated by all the detectors at the detector angles from $-\delta$ to $+\delta$ for the projection angle $\beta$. Asymmetric detector systems are also well known.

During a scan, the disk 16 rotates smoothly and continuously around the object being scanned, allowing the scanner 10 to generate a set of projections $P_f(\beta, \gamma)$ at the corresponding set of projection angles $\beta$. In a conventional scan, the patient remains at the constant z-axis position during the scan. When obtaining multiple scans, the patient is stepped along the z-axis between scans. These processes are commonly referred to as "step-and-shoot" scanning or "constant-z-axis" (CZA) scanning. Using well-known algorithms, such as the inverse Radon transform, a tomogram may be generated from a set of projections that all share the same scanning plane normal to the z-axis. This common scanning plane is typically referred to as the "slice plane."

A tomogram is a representation of the density of a two-dimensional slice along the slice plane of the object being scanned. The process of generating a tomogram from the projections is commonly referred to as "reconstruction," since the tomogram may be thought of as being reconstructed from the projection data. The reconstruction process can include several steps including convolution to deblur the data, rebinning to form parallel-ray data from the fan-beam-ray data and back projection in which image data for each image pixel is generated from the projection data. In CZA scanning, for a particular image slice, all the projections share a common scanning plane, so these projections may be applied directly to the back projector for generation of a tomogram.

The step-and-shoot CZA scanning approach can be a slow process. During this time consuming approach, the patient can be exposed to high amounts of x-ray radiation. Also, as the scanning table is moved between each scan, patient motion can result, causing motion and misregistration artifacts which result in reduced image quality.

Several approaches have been developed to decrease the time required to obtain a full scan of an object. One of these approaches is helical or spiral scanning in which the object being scanned is translated along the z-axis while the disk 16 with source 12 and linear detector array 14 are rotated about the patient. In helical scanning, the projections $P_f(\beta, \gamma)$ are normally acquired such that z is linearly related to the view angle $\beta$ so that $z(\beta) = c\beta$, where c is a constant. This form of helical scanning is commonly referred to as constant-speed-helical (CSH) scanning.

FIG. 3A illustrates the data collected during a conventional CZA scan, and FIG. 3B illustrates the data collected during a CSH scan. As shown in FIG. 3A, if the x-ray source 12 and the detector system 14 are rotated about the object 20 while the object remains at a fixed z-axis location, the scanning planes associated with all the projections collected by the detector system 14 will all lie in a common slice plane 50. As shown in FIG. 3B, if the object 20 is continuously translated in the direction of the z-axis while the disk is rotated about the object 20, none of the scanning planes will be co-planar. Rather, the scanning plane associated with each projection will lie at a unique position along the z-axis at a locus point on a helical set of loci. FIG. 3B illustrates the z-axis coordinate of the scanning planes corresponding to helical projection angles in the interval (0, 10π). Since the value of each projection depends on the z-axis location of the patient, each projection may be considered a function of two variables β and z.

In CZA scanning, all the projections share a common scanning plane, so these projections may be applied directly to the back projector to generate a tomogram. In CSH scanning however, each projection has a unique scanning plane located at a unique z-axis coordinate, so CSH projections may not be applied directly to a back projector. However, the data collected during a CSH scan can be interpolated in various fashions to generate a set of interpolated projections that do all share a common scanning plane extending normal to the z-axis. Each interpolated projection, for example, may be generated by combining two projections taken at equivalent projection angles and at different z-axis positions. These interpolated projections may be treated as CZA data and applied to a back projector to generate a tomogram.

CSH scanning requires some form of interpolation to generate a tomogram, and tomograms generated by CSH scanning therefore tend to be characterized by image artifacts. Also, since the CSH scan projection data, which are collected over an interval of z-axis locations, are combined to generate the interpolated CZA scan data, tomograms generated during CSH scanning have a wider effective slice plane width and, therefore, lower z-axis resolution, than tomograms generated by CZA scanning. However, helical scanning advantageously permits rapid scanning of a large volume of a patient. For example, in a time interval short enough to permit a patient comfortably to hold his or her breath (and thereby remain relatively motionless), a helical scan can collect enough data to fully scan an entire organ such as a kidney.

Another approach to decreasing scan time over CZA scanning is commonly referred to as "cone-beam scanning," in which a three-dimensional volume of the object or patient is scanned at once. In cone-beam scanning, the detection system includes a two-dimensional array of detectors instead of the one-dimensional array used in conventional scanning. The x-ray output from the source diverges in two dimensions to produce the equivalent of multiple fan beams along the z-axis dimension which illuminate multiple rows of plural detectors and therefore form a two-dimensional projection on the array.

In one form of a cone-beam system, the patient or object is maintained in a stationary z-axis position while the source and two-dimensional detector array are rotated around the patient or object. The patient is then moved to a new z-axis position, and the scan is repeated. In this type of step-and-shoot or "stationary cone beam" system, rather than sweeping out a plane, a volume of the object is scanned. After one volume is scanned, the source and detector are stepped along the z-axis to scan the next volume. Still another approach used to decrease scan time is helical cone-beam (HCB) scanning, in which a cone-beam configuration, i.e., a source and two-dimensional detector array, are rotated around the patient while the patient is continuously translated in the z-direction.

Standard two-dimensional reconstruction techniques, such as 2D filtered back projection (FBP), are used to reconstruct CZA and interpolated CSH data in non-cone-beam systems. FBP requires that the set of projections used for reconstruction lie in the same plane. This condition is satisfied in CZA scanning, and interpolation is used in CSH scanning to produce a set of interpolated or simulated linear projections which effectively meet this requirement. In either case, 2D FBP is an efficient means of producing image data from the 1D fan beam projection data.

In cone-beam geometry, the required condition is only satisfied for a detector row coplanar with the source in a plane perpendicular to the z-axis, i.e., the center detector row. In stationary cone-beam CT, a 1D projection defined by the source and a given detector row will intersect a different slice in the object as the gantry rotates. Conventional 2D FBP can be used to reconstruct cone-beam data by treating each row as an independent 1D projection. This approximation ignores the cone-beam geometry and results in image artifacts such as streaks and lowering of the reconstructed density. A better approximate method used to reconstruct cone-beam data is known as the Feldkamp algorithm and is described in L. A. Feldkamp, et al., "Practical cone-beam algorithm," *J. Opt. Soc. Am.* 1, pp. 612–619, (1984).

In the Feldkamp algorithm, the rays are back projected in the three-dimensional cone. Algorithms such as Feldkamp, which attempt to incorporate the true cone-beam geometry of the data, are referred to as three-dimensional filtered back projection (3D-FBP) algorithms. Three-dimensional algorithms reconstructing HCB data have also been developed. Examples of these algorithms are described in the following papers.

1. H. Kudo and T. Saito, "Three-dimensional helical-scan computed tomography using cone-beam projections," *Journal of Electronics, Information, and Communication Society*, J74-D-II, 1108–1114, (1991).
2. D. X. Yan and R. Leahy, "Cone-beam tomography with circular, elliptical and spiral orbits," *Phys. Med. Biol.* 37, 493–506, (1992).
3. S. Schaller, T. Flohr and P. Steffen, "New efficient Fourier reconstruction method for approximate image reconstruction in spiral cone-beam, CT at small cone angles," *SPIE International Symposium on Medical Imaging*, February, 1997.
4. G. Wang, T-H Lin, P. Cheng and D. M. Shinozaki, "a general cone beam algorithm," *IEEE Trans. Med. Imag.* 12, 486–496, (1993).

A disadvantage of 3D reconstruction algorithms is that they cannot be used with common 2D reconstruction hardware, and, consequently, custom 3D back projection hardware must be built to accommodate them.

OBJECTS OF THE INVENTION

It is an object of the present invention to substantially overcome the above-identified drawbacks of the prior art.

Another object of the invention is to provide a CT system with reduced image artifacts.

Yet another object of the invention is to provide a CT system which provides the image quality of a three-dimensional reconstruction algorithm using two-dimensional reconstruction hardware.

Still another object of the invention is to realize the foregoing objects in a helical cone-beam scanning CT system.

SUMMARY OF THE INVENTION

Accordingly, the present invention is directed to a CT apparatus and method for generating image data for a region. The region defines a longitudinal axis and an orthogonal transverse axis. A radiation source and an array of detectors are used to scan the region to generate scanned data that is representative of the region. In one embodiment, a helical cone-beam scanning approach is used to scan the region. At each of a plurality of positions along the longitudinal axis, or, equivalently, at each of a plurality of projection angles, a two-dimensional image data slice is defined. Each data slice defines a slice plane which is tilted with respect to the longitudinal axis of the region. That is, the normal axis of each slice plane is tilted at a tilt angle with respect to the longitudinal axis of the region. The normal axis also defines a rotation angle with the transverse axis of the region. Successive slices along the longitudinal axis define normal axes that define equal tilt angles with the longitudinal axis of the region. Also, the rotation angle for successive slices increases along the longitudinal axis. The result of the constant tilt angle and increase in rotation angle is that the normal axes describe a precession and nutation about the longitudinal axis of the region through successive slices. In this geometry, the slices can be said to be nutated with respect to each other. At each of the image slices, image data is computed from the scan data to produce the image of the region. The reconstruction process for successive slices is hereinafter referred to as the "nutating slice reconstruction" (NSR) approach.

The NSR approach of the invention is preferably used to reconstruct helical cone-beam data using conventional two-dimensional filtered back projection. In NSR, a set of 1D fan-beam projections is extracted from the 2D cone-beam projection data set using interpolation. NSR therefore involves the selection of 2D fan-beam data from 3D cone-beam data. The 1D projection set corresponds to reconstructing a tilted slice whose geometry is chosen to minimize the adverse effects of the cone angle on image quality when using 2D FBP.

Traditionally, when reconstructing a series of slices, each slice is the x-y plane at a different location along the z-axis. That is, all the slices in the series are parallel to each other. In NSR, the normal vector to the reconstructed slice plane is tilted by a small angle with respect to the z-axis. In a series of adjacent slices reconstructed with NSR, the normal vector to the slice plane precesses about the z-axis and the slices are not parallel to each other. The term "nutated" in NSR refers to the relative orientation of adjacent slices. If parallel slices are required, the resultant NSR image data can be interpolated to provide parallel slices.

In one embodiment, the x-ray source is a cone-beam source, and the array of detectors is a two-dimensional array. The scan data for each projection is determined from a predefined one-dimensional line of detectors on the array. The detectors used for a given projection or slice are associated with the projection angle or position along the longitudinal axis. At each position or projection angle, a group of detectors is chosen which minimizes the error in the measurement. Each slice is therefore associated with a projection angle, a longitudinal position and a group of detectors which in general defines a one-dimensional "fan-beam" projection on the two-dimensional detector array. When a particular slice is reconstructed, its scan data is generated from its associated detectors in the two-dimensional array.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE DRAWINGS

Figure 4:
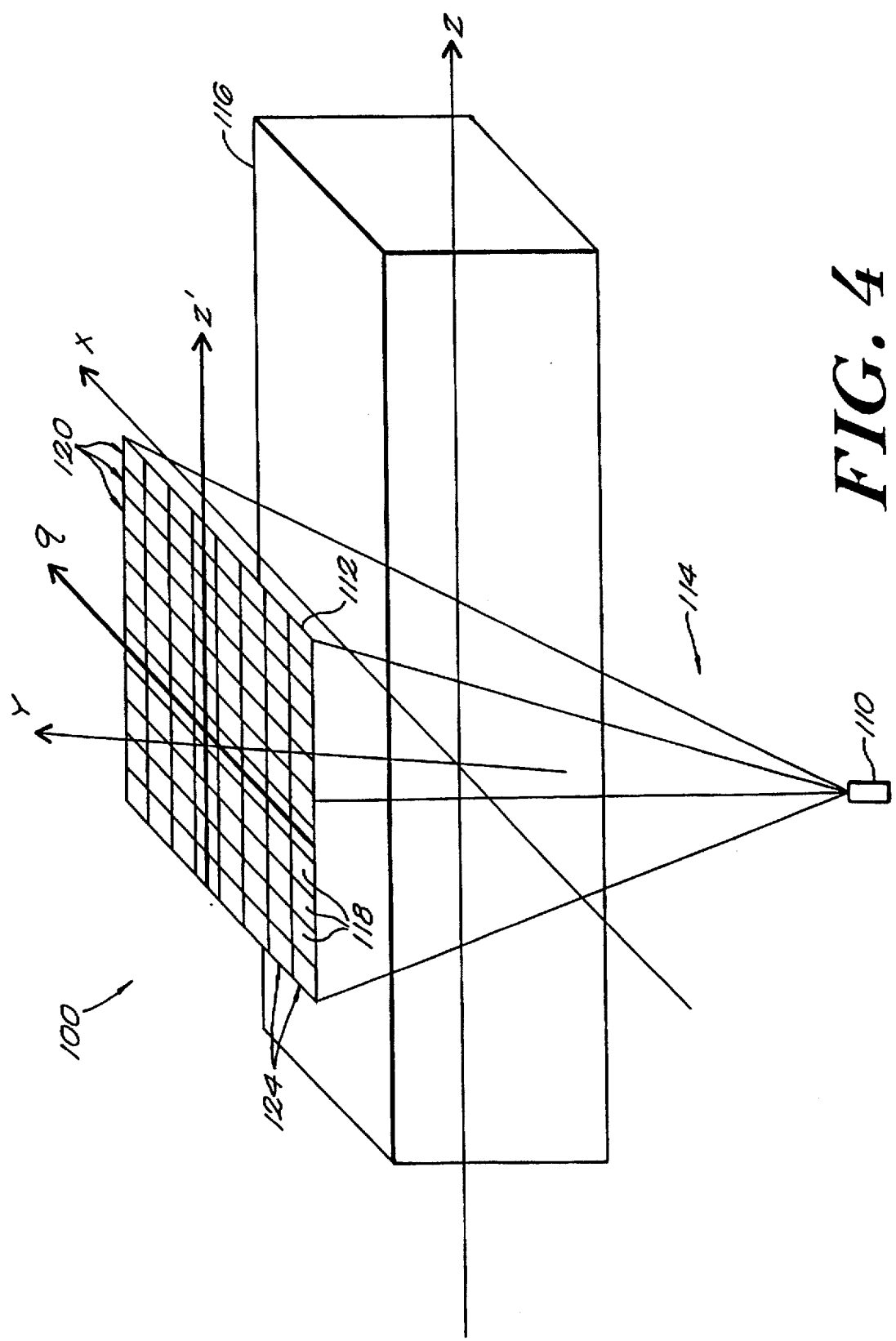
FIG. 4 is a simplified schematic diagram which illustrates the spatial relationships among the source, detectors and scanning object in a CT scanner in accordance with the present invention.

FIG. 4 is a schematic diagram which illustrates the functional operation of one embodiment of the CT scanning system 100 of the invention. The system includes an x-ray source 110 which emits x-rays toward a two-dimensional x-ray detector array 112. The detector array 112 is shown as a flat array having coordinates z' and q. A curved array can also be used. The x-rays diverge in a cone-beam which passes through an object 116 being scanned. The x-rays, attenuated by the object 116, are detected by the individual detectors 118 in the detector array 112. The array 112 of detectors includes multiple rows 120 of detectors along the z'-axis and multiple columns 124 along the q-axis. The cone-beam 114 therefore can be considered to consist of multiple fan beams spread along the q-axis and adjacent to each other along the z'-axis. The object 116 defines a z-axis (also referred to herein as the longitudinal axis) and an orthogonal x-axis (also referred to herein as the transverse axis).

As discussed above, the x-ray source 110 and detector array 112 are secured to diametrically opposite sides of an annular shaped disk (not shown). The disk is rotatably mounted within a gantry support (not shown) such that the source 110 and detector array 112 are simultaneously rotatable about the z-axis and, hence, about the object 116 being scanned.

In one embodiment, the system 100 uses helical cone-beam scanning such that, as the gantry rotates about the z-axis, the gantry and object 116 are also translated relative to one another along the z-axis. The gantry with source and detector array rotate through an increasing projection angle β as the gantry translates along the z-axis. At each projection angle, scan data are collected by the detector array. Image data in the form of a series of image slices are then reconstructed from the projection data. Each slice defines a planar configuration of image data and is generated from a predefined collection of scan data gathered as the source and detector array rotate.

In the present invention, even though a three-dimensional scanning approach, namely, helical cone-beam scanning, is used, a two-dimensional reconstruction approach can be used to generate the image data. To accomplish this, the present invention projects a two-dimensional data slice onto the two-dimensional array of detectors such that the projection of the slice at each projection angle can be considered a one-dimensional fan beam projection. In the general case, the projection onto the array falls on a group of detectors which are not necessary in a single row or column. In fact, in general, the projection will extend across several rows and columns. In the present invention these rows and columns are identified for each projection angle. A value is generated for each location at each projection angle from the projection data, in one embodiment, by interpolating the projection data. Thus, for each projection angle, a "fan beam" of detector data is generated, very much analogous to the fan beam data generated in two-dimensional fan beam scanning applications which use a linear detector array. The result is a set of "fan beam" data for each projection angle. In the present invention, once these data are generated, they can be applied to any suitable two-dimensional back projection algorithm to reconstruct image slices as if it were actual fan beam data.

In the present invention, at each projection angle the rows and columns of the detector array which receive the associated fan beam are identified before an actual scan is performed. In one embodiment, a simulation or calibration scan, which simulates helical cone-beam scanning of an opaque disk, can be performed. At each projection angle, the simuated projection of the disk onto the array is recorded in the detector data. After the disk is entirely scanned, the projection data is analyzed to determine which rows and columns of the array receive the projection of the disk at each projection angle. The simulation process creates a "z-interpolation table" in which each projection angle is associated with a group of detector rows and columns which should be read during subsequent scans of actual objects to generate the 1D fan beam data. When the desired slices are reconstructed, the fan beam data at each projection angle are detected from the associated array row and columns stored in the z-interpolation table. In another embodiment, an actual opaque disk can be subjected to helical cone-beam scanning with an actual source and detector array to generate the z-interpolation table.

Many fan beam projections are collected for each slice to be reconstructed. For example, in one embodiment, data is collected for one half of a complete revolution of the gantry (180°) plus the angle subtended by the detector array. In one embodiment, the array subtends a 60° angle; hence, each slice is generated from data collected during 240° of gantry revolution. In one embodiment, projections are produced every 1° of projection angle. Therefore, in this embodiment, each slice is generated from 240 fan beam projections. The groups of projections for successive slices along the z-axis can overlap each other. For example, slices may be generated every 12° of rotation. Therefore, in the embodiment described above, 228 out of 240 projections are shared by each pair of adjacent slices.

As mentioned above, in general, the reconstructed slices in the present invention are not perpendicular to the z-axis as in conventional non-cone-beam scanning. Instead, they are tilted or nutated with respect to the z-axis, and the normal axes of successive slices precess about the z-axis. Each slice defines a slice plane having a normal axis which forms an angle with the longitudinal or z-axis about which the scanning system rotates. The use of a tilted slice reduces the error in the reconstructed slice data. The angle of tilt can be determined using the simulation scan mentioned above and also described below in more detail. The selected angle is the angle at which the projection of the opaque disk onto the array produces the least image reconstruction error.

Figure 5:
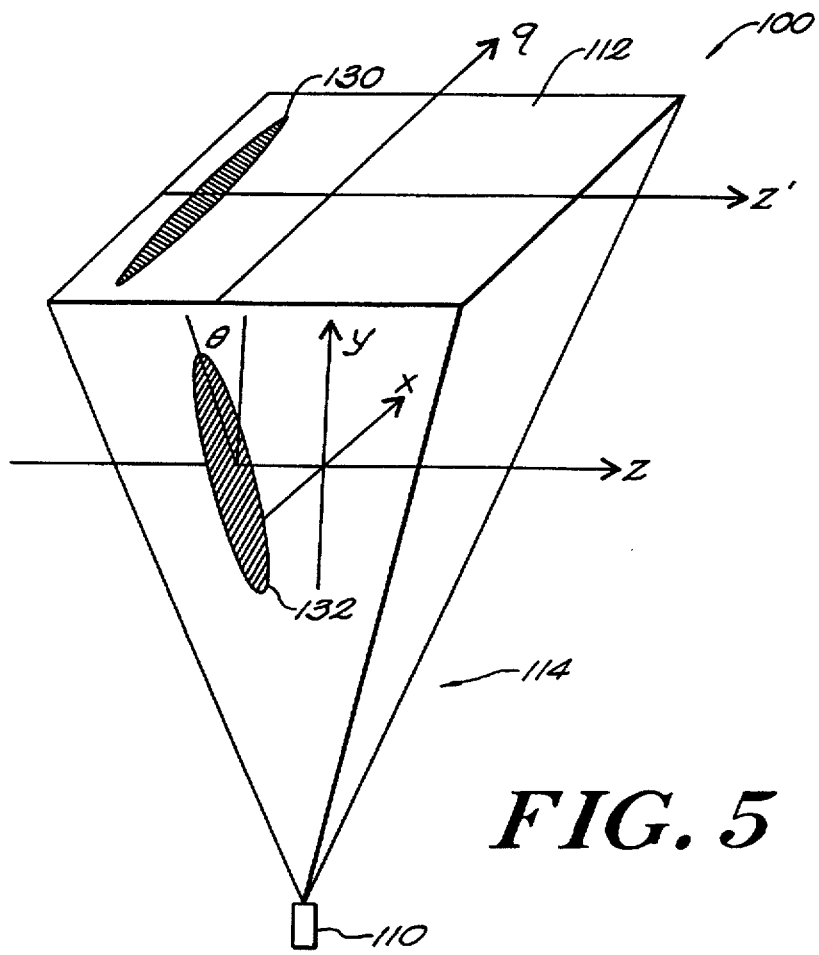
FIG. 5 is a simplified schematic illustration of the projection of a tilted slice onto a two-dimensional detector array.

FIG. 5 is a schematic diagram which illustrates acquisition of data during the simulation scan for a single projection at a single angle using a tilted reconstruction image slice represented by the titled opaque disk 132. The cone beam of x-rays 114 is emitted by the source 110 and passes through the object (not shown) and illuminates the flat two-dimensional detector array 112. As shown, the plane of the slice or disk 132 forms an angle θ with an axis orthogonal to the z-axis. Equivalently, the normal axis to the slice plane forms the angle θ with the z-axis.

An elliptical projection or shadow 130 of the tilted disk 132 is projected onto the detector array 112. As the source 110 and detector array 112 rotate about and move along the z-axis, the location and shape of the projection 130 of the disk 132 changes. As the disk 132 moves through the scanning volume, or, equivalently, as the source and detector are scanned past the slice, the area of the projected ellipse changes. The tilt angle θ is fixed as the disk 132 translates through the detector array.

The spread of the ellipse (the length of its minor axis) at each projection angle is an indication of the error introduced in reconstructing the slice at that projection angle. The object is to select a disk geometry that minimizes the total projected ellipse area over all of the projection angles, e.g., 240°, for the tilted slice being reconstructed. The area is minimized by reconstructing a tilted slice where the normal to the slice plane is tilted by a small angle θ.

Figure 6:
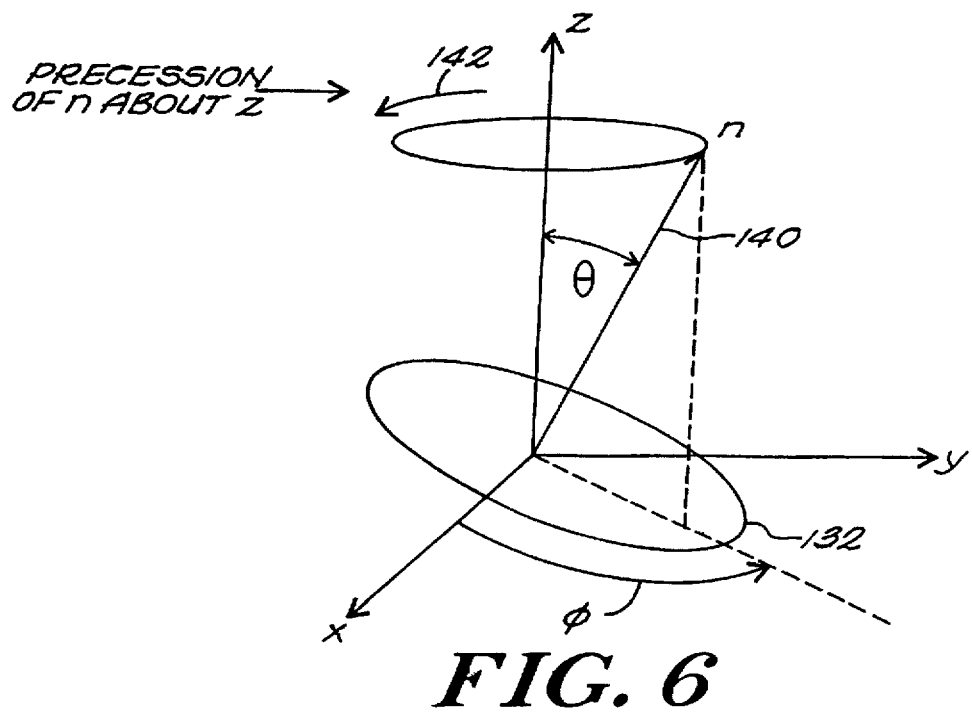
FIG. 6 is a simplified schematic illustration of the tilt and rotation angle of a tilted slice in accordance with the present invention.

FIG. 6 is a schematic diagram which illustrates the relationship between a tilted slice 132 and the system axes. As mentioned above, the normal 140 to the slice plane forms an angle θ with the z-axis, which is referred to herein as the tilt angle or nutation angle. The normal axis 140 also forms a rotation angle ø with the x-axis or transverse axis of the system.

As described above, each slice can be reconstructed from projections whose projection angles span the range of 0° to 180° plus the array angle (60°). At one degree per projection, each slice is reconstructed from 240 projections. For any given slice, a particular slice tilt angle θ and rotation angle ø will yield the smallest error over all 240 projections. In one embodiment, adjacent slices are reconstructed every twelve degrees of rotation from overlapping sets of 240 projections shifted by twelve degrees. Each slice is associated with a tilt angle θ and rotation angle ø which minimize the reconstruction error in the slice. In one embodiment, for successive slices, the tilt angle θ remains constant and the rotation angle ø increases or decreases to define a rotation or precession of the normal axes of slices about the z-axis, as illustrated by the arrow 142 in FIG. 6. The error at each tilt angle is determined by summing the total area of all disk projections over the entire 240° of data. The tilt angle yielding the minimum total error is taken as the tilt angle. In one embodiment, a tilt angle of approximately 1.45° is used.

Figure 7:
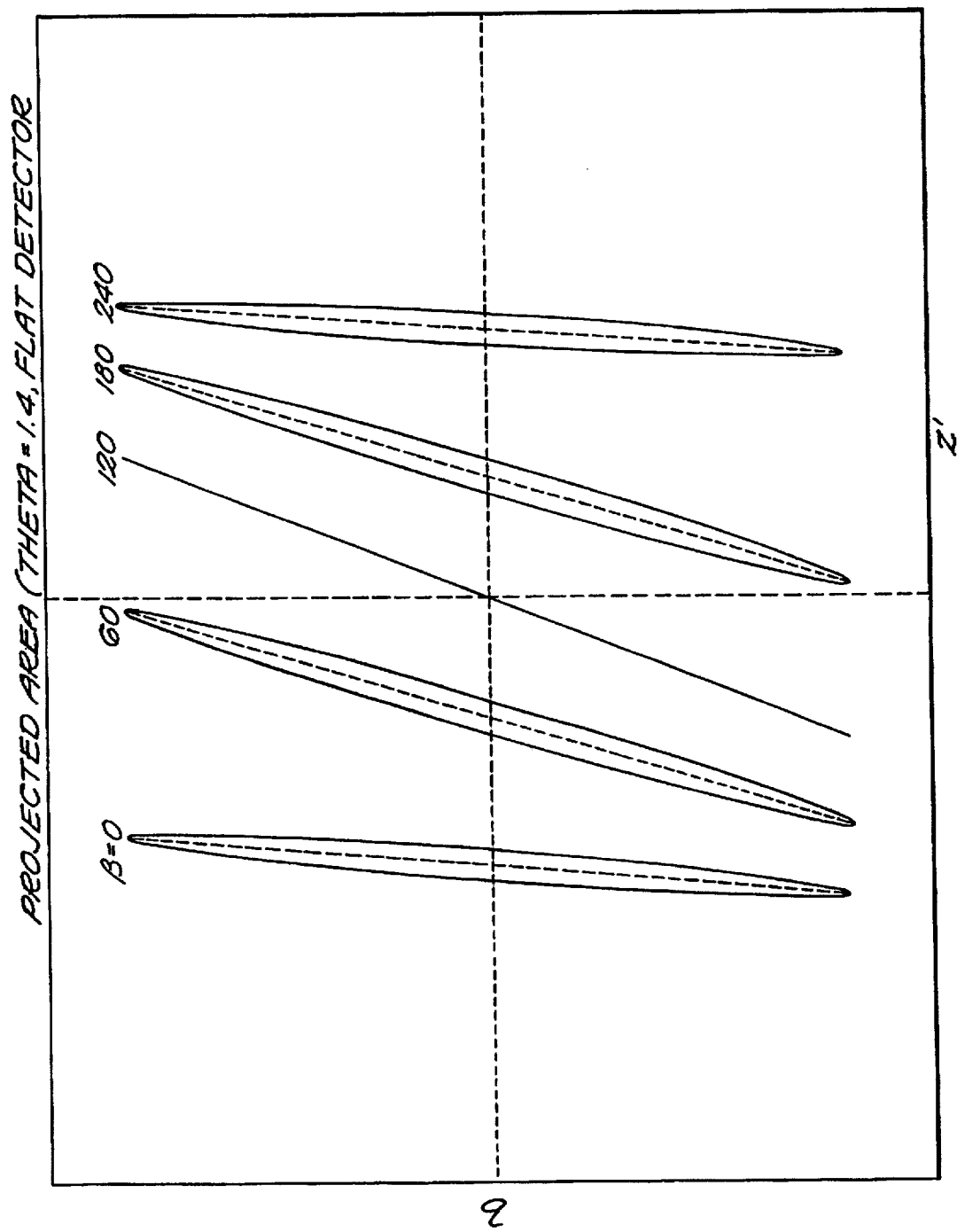
FIG. 7 is a simplified schematic diagram of projections of a tilted slice onto a flat detector array.

FIG. 7 is a schematic diagram showing projections of the disk 132 at a tilt angle of 1.4° passing through the scan region. The curves show projections at projection angles of β=0°, 60°, 120°, 180°, and 240°. The figure assumes a flat detector array.

Figure 8:
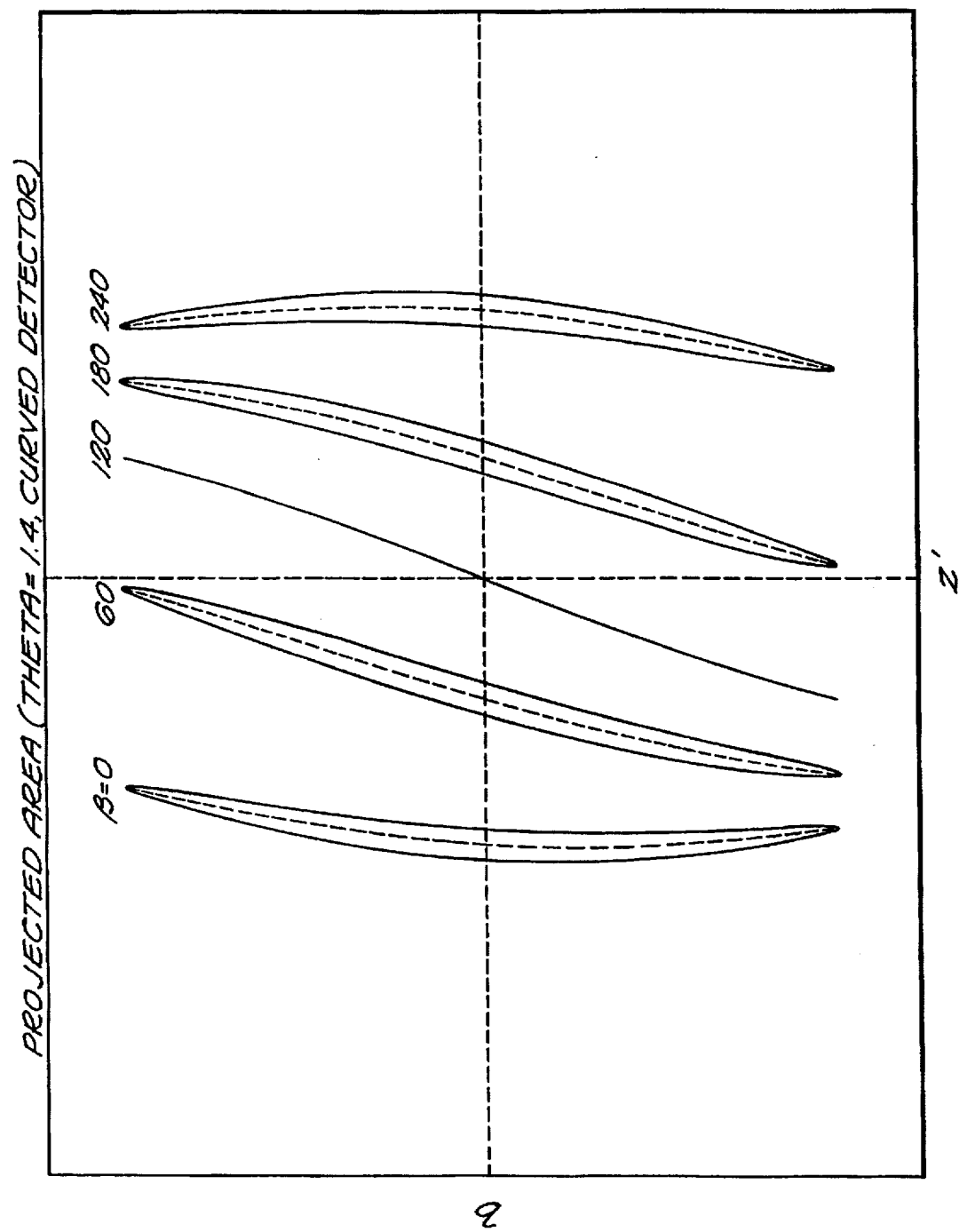
FIG. 8 is a simplified schematic diagram of projections of a tilted slice onto a curved detector array.

As noted above, the detector array can also be curved. In that case, the projections of the disk or slice onto the array will not be ellipses as shown in FIG. 7. They will actually be curved figures as shown in FIG. 8. FIG. 8 shows the same projections as FIG. 7 with a tilt angle of 1.4°, except that the detector array 112 is curved.

Figure 9:
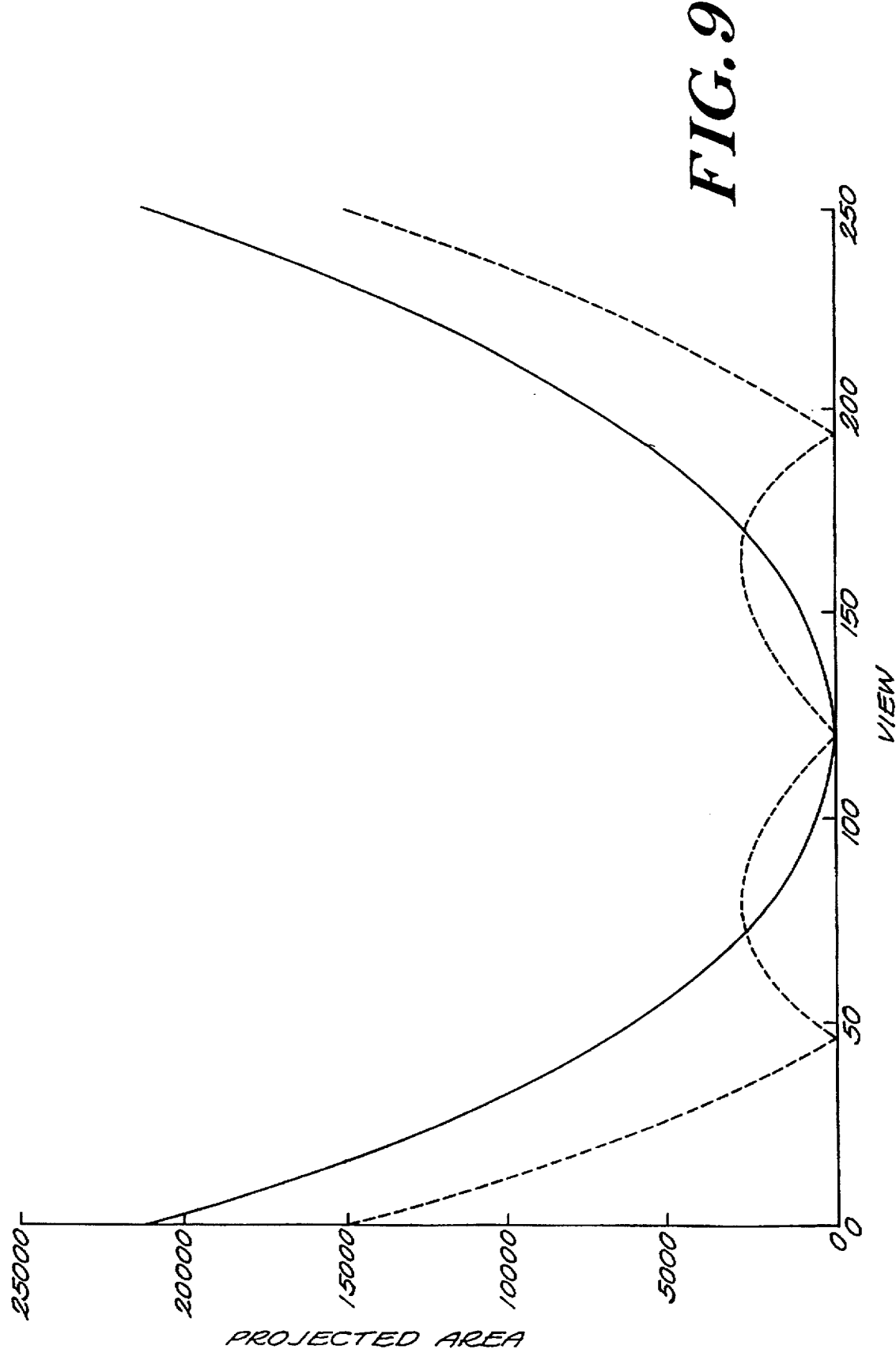
FIG. 9 contain schematic plots of the total projected area of a tilted slice and a perpendicular slice versus view angle.

An example of the total projection area plotted as a function of view is shown in FIG. 9. The dashed line shows the area for a tilt angle of 1.45° and the solid curve shows the area for no tilt angle. The tilt angle is chosen as the angle which minimizes the total area, which in one embodiment is determined to be 1.45°.

Figure 10:
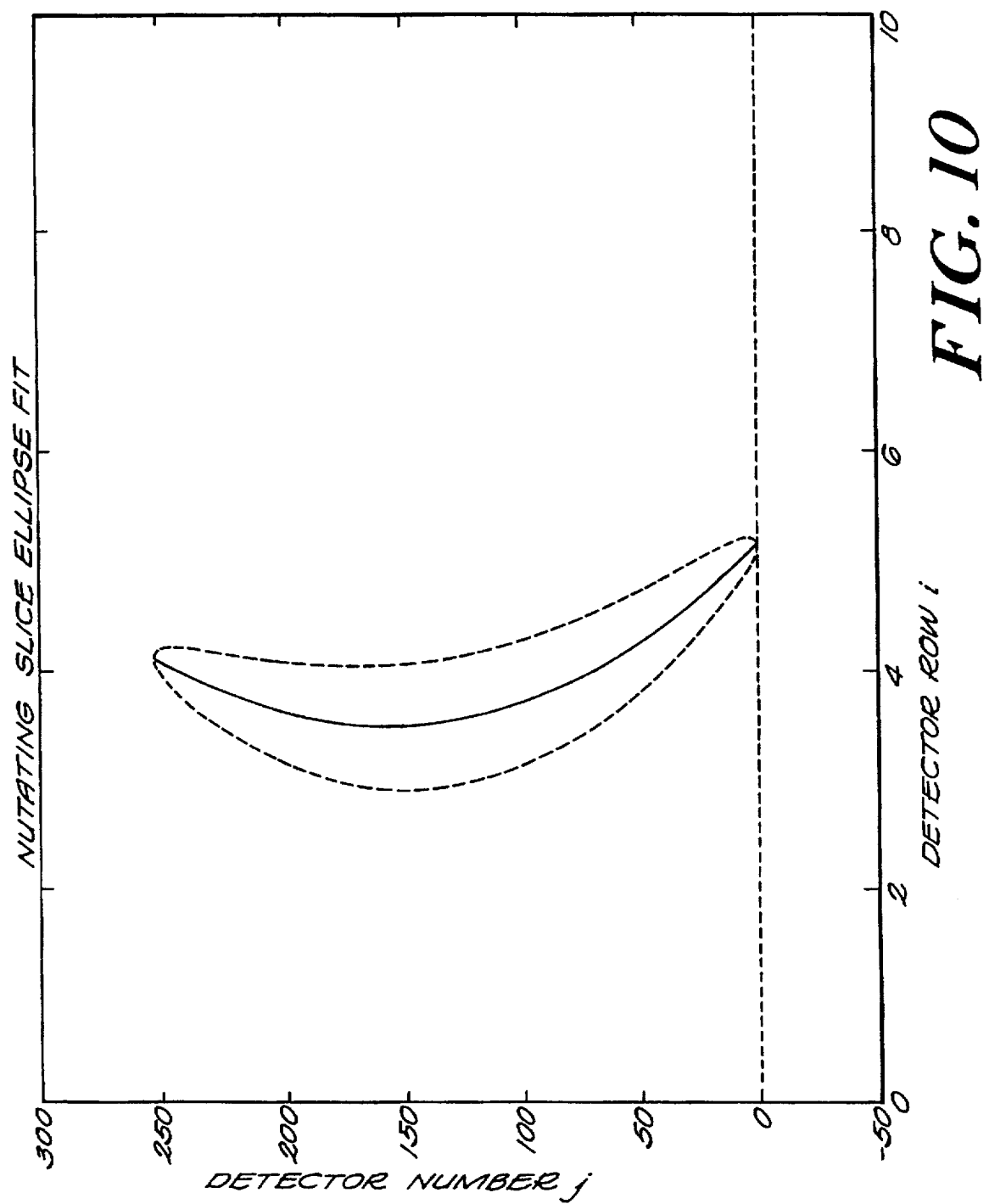
FIG. 10 is a simplified schematic diagram of a slice projection onto a curved detector array.
Figure 11:
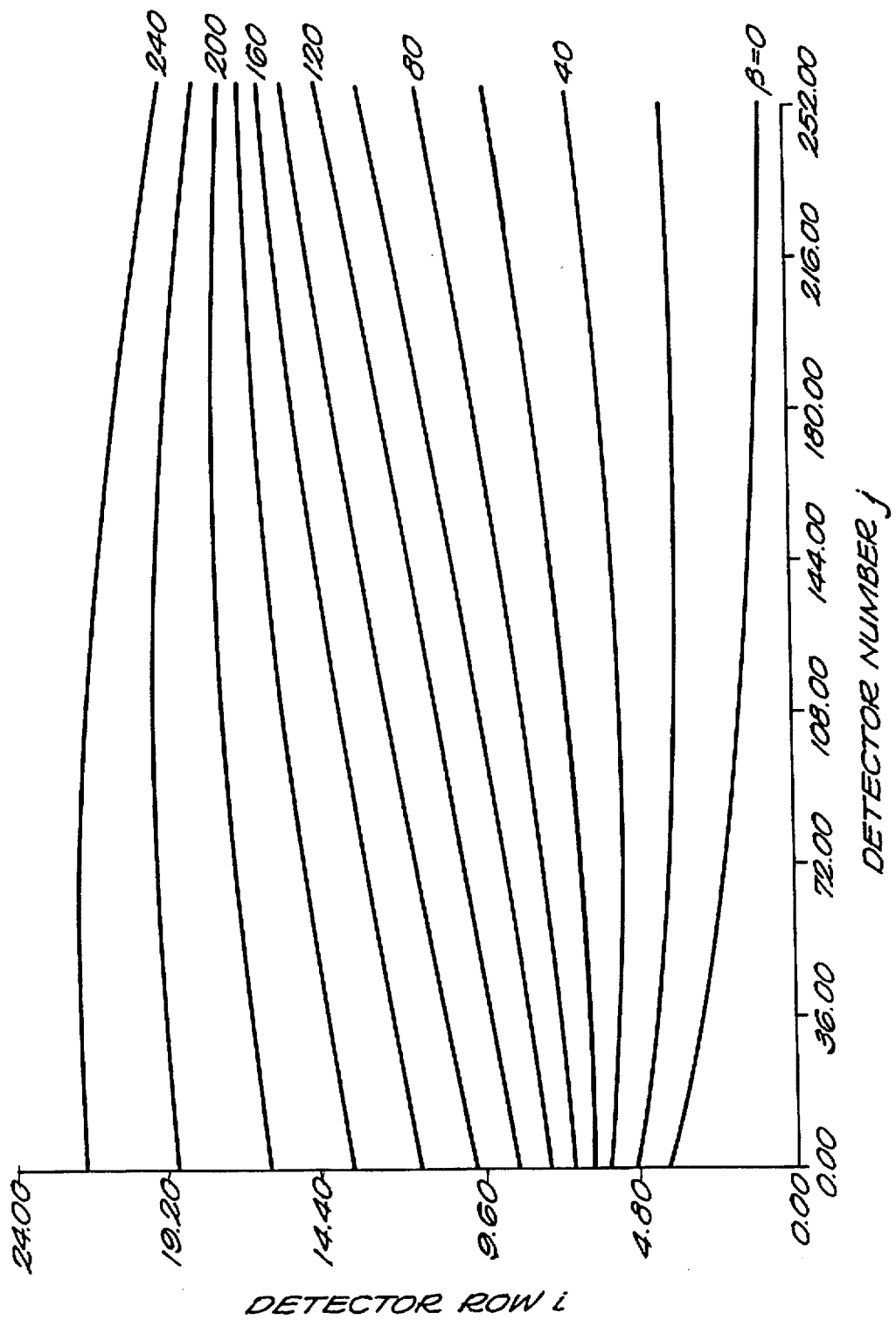
FIG. 11 is a simplified diagram showing slice projection lines on a two-dimensional curved array for projection angles between 0° and 240°, in increments of 20°.

As described above, the simulation scan can also be used to identify the pixel rows and columns used for each projection at each different projection angle. FIG. 10 is an example of a single tilted slice projection onto the curved detector array. All of the detectors on the array are read to identify the location of the projection 150 and, therefore, the detector rows and columns which should be read during future scans of actual objects at the particular projection angle. In this embodiment, the array includes ten rows i of 252 detectors j each. The dashed line 150 indicates the spread of the curved elliptical projection on the array. The solid line 152 identifies the line of detectors that are read during subsequent scans at this particular projection angle. The line 152 is identified by computing the centroid of the detector values across each row. It is this solid line 152 that defines the detectors to be read during subsequent scans of an actual object. This process is completed at each projection angle for the slice to be reconstructed. The simulation or calibration process associates each projection angle with a row and column value and stores them together in a "z-interpolation table." This table is read during subsequent scans to identify the scan data used to reconstruct actual slices. FIG. 11 shows a set of disk projections on a two-dimensional curved array for a slice tilted at 1.45° at view angles between 0° and 240°, spaced by 20° each. These are the array row/column lines generated for each projection angle during the calibration scan. The row/column numbers plotted for each projection angle are stored in the z-interpolation table. The array used for this plot is a standard array consisting of 24 detector rows i of 252 detectors j each. As described above, each of the curved lines is identified by computing the centroid of the projection on the array at each view angle.

After the simulation scan is performed as described above to generate the z-interpolation table, actual scans of objects can be performed according to the following procedure. First, the projection data can be obtained by helical cone-beam scanning. Next, the projection data can be corrected for offsets, gain error and non-linear effects. Next, the HCB data is applied to the z-interpolation process, which extracts the desired fan-beam data. At each projection angle, detector row and column numbers are retrieved from the z-interpolation table, and x-ray intensity values at the identified detector rows and columns are recorded as the fan-beam data. In one embodiment, the z-interpolation process can proceed as follows: At each view, the process steps through each detector j, one at a time. For each detector, a row number I is identified from the z-interpolation table, which is in general some real number. Where the row number i is not a whole number, interpolation can be performed on the actual data values at the appropriate row numbers to identify a value for the particular detector as described below. In one embodiment, linear interpolation is used, but other forms of interpolation can be used.

For the remainder of the reconstruction process, the interpolated data values can be treated as if they were fan beam values obtained during a conventional two-dimensional scanning procedure. They can optionally be applied to a rebinning process to produce parallel-ray data. The rebinned two-dimensional data can then be applied to a conventional one-dimensional convolution procedure. Finally, the parallel-convolved data can be applied to a conventional two-dimensional back projection algorithm. The above process is repeated for each slice in the region.

A detailed mathematical description of the approach of the invention follows.

Let a continuous cone beam data set be given by $C(\beta,z',q)$, where $\beta$ is the gantry rotation angle (or view angle), and q and z' are the position on the detector as shown in FIG. 4. To reconstruct one slice, the angular range of $\beta$ must be at least 180° plus the fan angle. A reconstruction using the minimum number of projections is referred to as a halfscan. Let $\beta_h$ be the range of projection angles used for halfscan reconstruction. More views can be used if an overscan correction is desired. The method of overscan is discussed in detail below.

The method of NSR can be summarized as follows:

1. For a given $\beta$, where $0 \leq \beta < \beta_h$, extract a fan beam projection, $F(\beta,q)$, from the cone beam data $C(\beta,z',q)$. The fan beam data are given by $$F(\beta,q)=C(\beta,L(\beta,q),q) \qquad (1),$$

where $L(\beta,q)$ is the line of the desired 1D projection $(z'=L(\beta,q))$. $F(\beta,q)$ may optionally be rebinned to parallel data at this stage. The rebinning is the preferred method due to the computational efficiency of backprojecting parallel views rather than fan views. The rebinning procedure is discussed in detail below.

2. Convolve $F(\beta,q)$ with an appropriate convolution kernel.

3. Backproject the convolved data using 2D-FBP.

The method of determining $L(\beta, q)$ and the optimization of the tilt angle are discussed below.

In reality, the cone beam data does not exist in continuous form and a method for discrete implementation is used. Specifically, the data on the line $L(\beta,q)$ must be determined by interpolating from discrete detectors. Let the cone beam data be given by $C[v,r,d]$, where v is the view number (in the $\beta$ direction), r is the detector row number (in the z-direction), and d is the detector channel number (in the q-direction) in a given row. Also let the limits be defined as $0 \leq v < N_h$, $0 \leq r < N_r$, and $0 \leq d < N_d$, where $N_h$ is the number of half scan views, $N_r$ is the number of rows, and $N_d$ is the number of detectors per row. The relations between the discrete and continuous variables are $$\beta=v\Delta_\beta \qquad (2)$$

$$z'=(r-r_c)w_r \qquad (3)$$

$$q=(d-d_c)w_d \qquad (4)$$

where $\Delta_\beta$ is the angle between views, $w_r$ is the distance between rows, $w_d$ is the distance between detectors in a given row, $r_c$ is the row location of z'=0 and $d_c$ is the detector channel location of q=0.

$$r_c = N_r - 1/2 \quad (5)$$

$$d_c = N_d - 1/2 \quad (6)$$

As in the continuous case, the desired data lies along a line which intersects the ellipse. Let F[v,d] be the fan beam data selected from C[v,r,d]. The interpolation in the r direction is referred to as the z-interpolation. Let r'[v,d] be a lookup table which gives the location of the desired point in r for a given v and d. The fan data can be obtained by using linear interpolation in r. Namely, $$F[v,d] = (1-p)C[v,r_0,d] + pC[v,r_0+1,d] \quad (7)$$

where $r_0$ is the largest integer value less than or equal to r', and $p = r' - r_0$.

The z-interpolation table can be determined by simulating projection data for the simulated tilted disk, as described above. The simulated disk has thickness equal to the detector row width projected to the isocenter. The attenuation coefficient is constant throughout the disk, and the photon energy is monoenergetic. In this way, a given projection ray measured through the disk is directly proportional to the thickness traversed. The center of the disk is located at the isocenter and oriented with a fixed tilt angle θ. The disk travels in the z-direction at the specified table speed of the scanner. The location of the disk's center at the beginning and the end of data collection (i.e., at v=0 and $v=N_h-1$) is symmetric about z=0. The radius of the disk is equal to the scan radius R given by $$R = r_s \sin \delta \quad (8)$$

where $r_s$ is the distance from source to isocenter and δ is half the fan angle given by $$\delta = \frac{\Delta_\gamma N_d}{2} \quad (9)$$

where $\Delta_\gamma$ is the angle between detectors in a given row. The full detector width in the z-direction at isocenter is given by $$D = w_r N_r (r_s/r_d) \quad (10)$$

where $r_d$ is the distance from the source to the detector. We define the pitch, p, as the ratio of the table translation in 360 degrees of gantry rotation to D. Namely, $$p = \frac{s_t T}{D} \quad (11)$$

where $s_t$ is the table speed and T is the gantry rotation period. For example, for a pitch of one, the table moves a distance D in one rotation.

The simulation can use the same geometry of the scanner. Alternatively, the simulation can use more detector rows to improve the resolution in determining the z-interpolation table. See Table 1.

TABLE 1

| Parameter values and definitions. | |
|---|---|
| $N_d$ | Number of detector channels per row |
| $N_r$ | Number of rows |
| $N_h$ | Number of half scan views per image |
| $N_v$ | Number views per rotation |

TABLE 1-continued

| Parameter values and definitions. | |
|---|---|
| $N_m$ | Number of rows in simulation |
| $\Delta_\beta$ | Number of degrees per view |
| $\Delta_\gamma$ | Angle between detector channels in a row |
| $\Delta_{vj}$ | Slice separation in views |
| D | Full width of detector array at isocenter in z |
| R | Scan radius |
| $w_d$ | Distance between detector channels in q |
| $w_r$ | Distance between detector rows z |
| $w_{diso}$ | Distance between detector channels in q at isocenter |
| $w_m$ | Distance between detector rows in z used in simulation |
| $r_s$ | Distance from source to isocenter |
| $r_d$ | Distance from source to center of detector array |
| $s_t$ | Table velocity |
| T | Gantry rotation period |
| p | Pitch |
| θ | Tilt angle |

As mentioned above, the interpolation line is determined by computing the centroid in the row direction of the resultant projection data. Let m be the simulation row index where $$0 \leq m < N_m \quad (12)$$

The interpolation point m'[v,d], is given by calculating the centroid as follows:

$$m'[v,d] = \frac{\sum_{m=0}^{N_m-1} mC[v,m,d]}{\sum_{m=0}^{N_m-1} C[v,m,d]} \quad (13)$$

The value of m'[v,d] is then converted into the true detector row variable r'[v,d] where ($0 \leq r' < N_r$). The z'-location of m' is given by $$z' = (m' - m_c)w_m \quad (14)$$

where $m_c$ is the row location of z'=0 and $w_m$ is the distance between detectors in a given row in the simulation. The value of r' is then obtained by substituting Equation (14) into Equation (3) for z' and solving for r, which gives $$r'[v,d] = \frac{w_m}{w_r}(m'[v,d] - m_c) \quad (15)$$

The z-interpolation table is a function of the tilt angle, the geometry of the scanner, and the pitch. The pitch is fixed by the table speed, the gantry rotational speed, and detector size per Equation (11). The tilt angle can be chosen by a method described below.

Let the range of views from the scanner be given by $$0 \leq v < \infty \quad (16)$$

A slice is reconstructed by using a set of $N_h$ views. To reconstruct a series of adjacent slices, Steps 1 through 3 above are repeated for a different set of $N_h$ views for each slice. Let j be the slice number in the series of $N_j$ slices, $0 \leq j < N_j$. Also let $v_{0j}$ be the first view for a given slice j such that a given slice j uses the views $v_{0j} \leq v < v_{0j} + N_h$.

$$v_{0j} = j\Delta_{vj} \quad (17)$$

where $\Delta_{vj}$ is the separation in views between adjacent slices. The fan data for slice j are extracted from the cone beam data as follows:

$$F[v_h,d] = C[v_j, r'[v_h,d], d] \quad (18)$$

where $$v_j = v_h + v_{oj} \quad (19)$$

and where $0 \leq v_h < N_h$. Note that the z-interpolation table can be the same for each slice.

The plane of a tilted slice can be described by two rotations. The first rotation is about the x-axis by an angle $\theta$ and the second rotation is about the z-axis by an angle $\phi$. The equation of the nutated plane is given by $$x \sin \phi \sin \theta + y \cos \phi \sin \theta + (z - z_0) \cos \theta = 0 \quad (20)$$

where $z_0$ is the location of the center of the plane in z (i.e., in FIG. 6, $z_0 = 0$).

Figure 1:
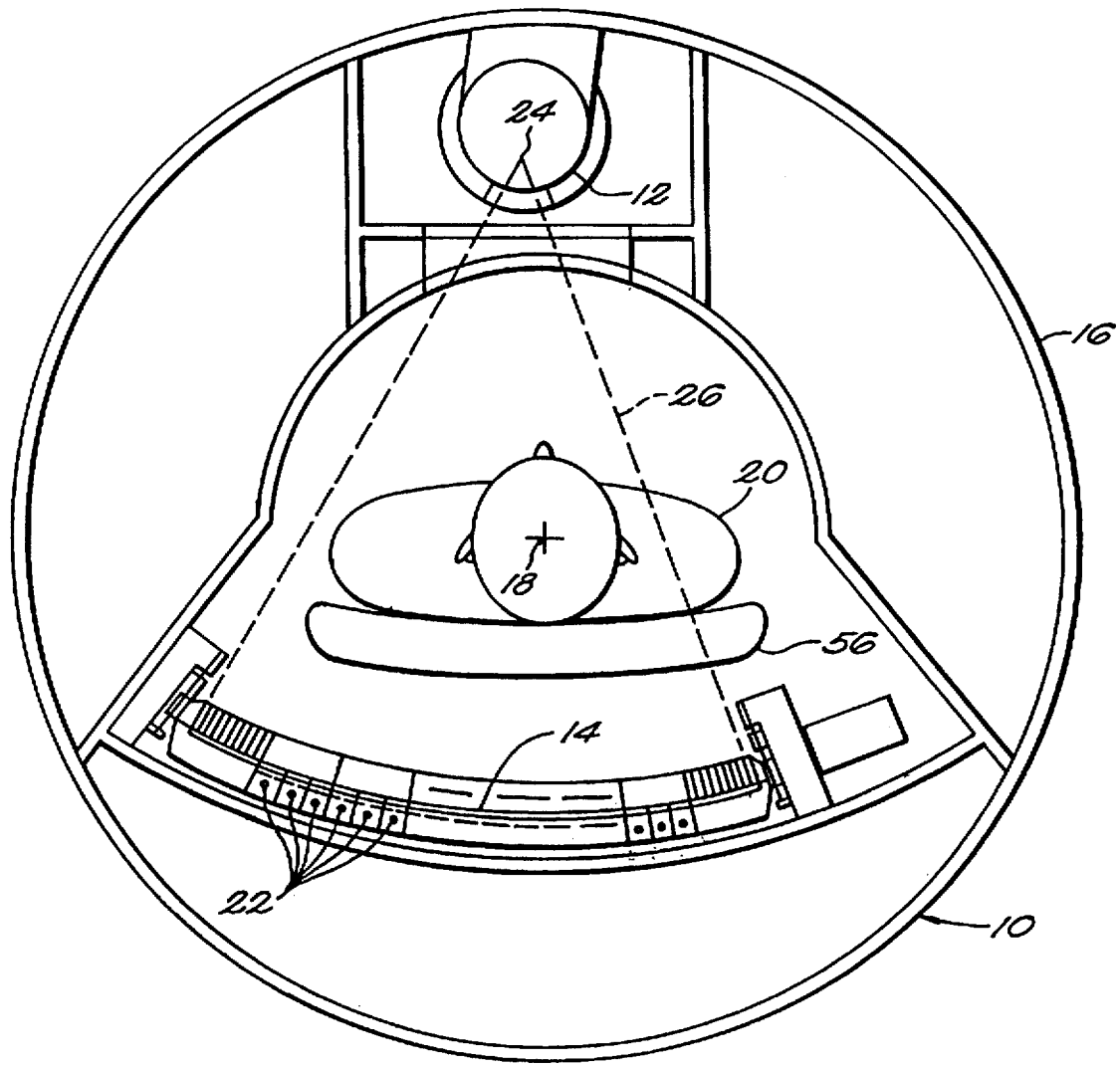
FIG. 1 is a schematic axial view of a typical conventional computed tomography (CT) scanner.
Figure 2:
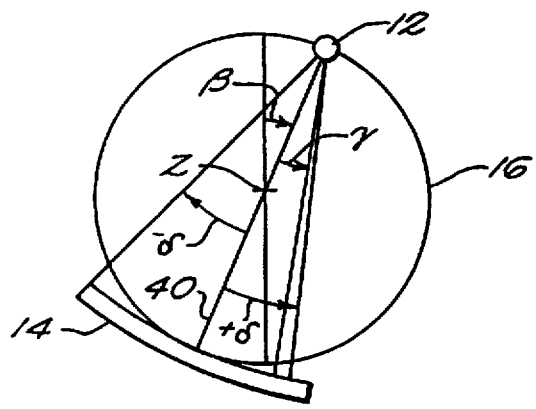
FIG. 2 is a schematic diagram which illustrates the projection angle and the detector angle of a CT scanning system.
Figure 3A:
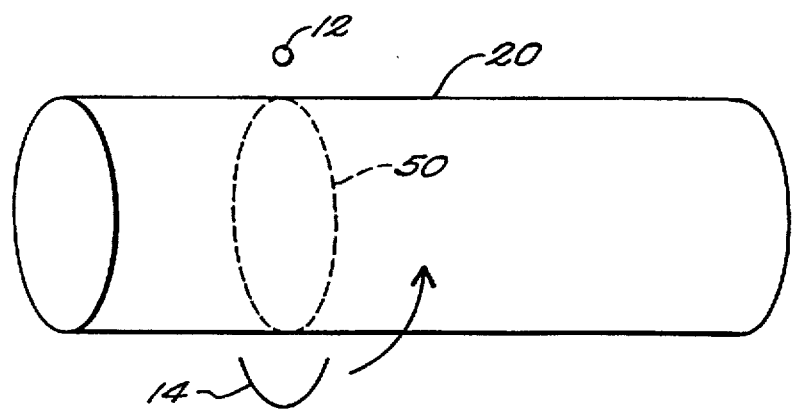
FIG. 3A illustrates the scanning path for a constant z-axis (CZA) scanning mode in a CT scanner.
Figure 3B:
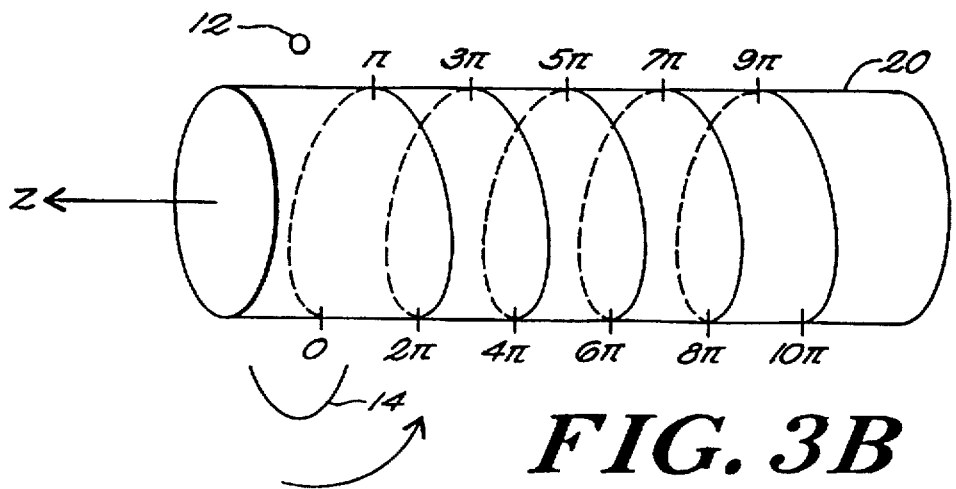
FIG. 3B illustrates the scanning path for constant-speed-helical (CSH) scanning in a CT scanner.

In a series of slices, the precession angle, $\phi$, is related to the view angle $\beta$. Let the gantry angle corresponding to $v_{oj}$ be denoted as $\beta_{oj}$. The precession angle for slice j is given by $$\phi_j = \beta_{oj} + \delta - \frac{\pi}{2} \quad (21)$$

where $\delta$ is half the fan angle as shown in FIG. 2 and defined in Equation (9).

The nutated slice geometry causes the slice separation in z to be a function of the location in x and y, as well as the pitch. At the center, $(x,y) = (0,0)$, the location in z is given by $$z_{oj} = \left( j - \frac{N_j - 1}{2} \right) \Delta_{z0} \quad (22)$$

where $\Delta_{z0}$ is the separation of slices at isocenter given by $$\Delta_{z0} = \Delta_{vj} \left( \frac{s_t T}{N_v} \right) \quad (23)$$

where $N_v$ is the number of views per rotation. In general, the separation at any point (x,y) is obtained by solving Equation (20) for z for two adjacent slice and taking the difference, namely, $$\Delta_{zj} = z_j - z_{j-1} \quad (24)$$

Figure 12:
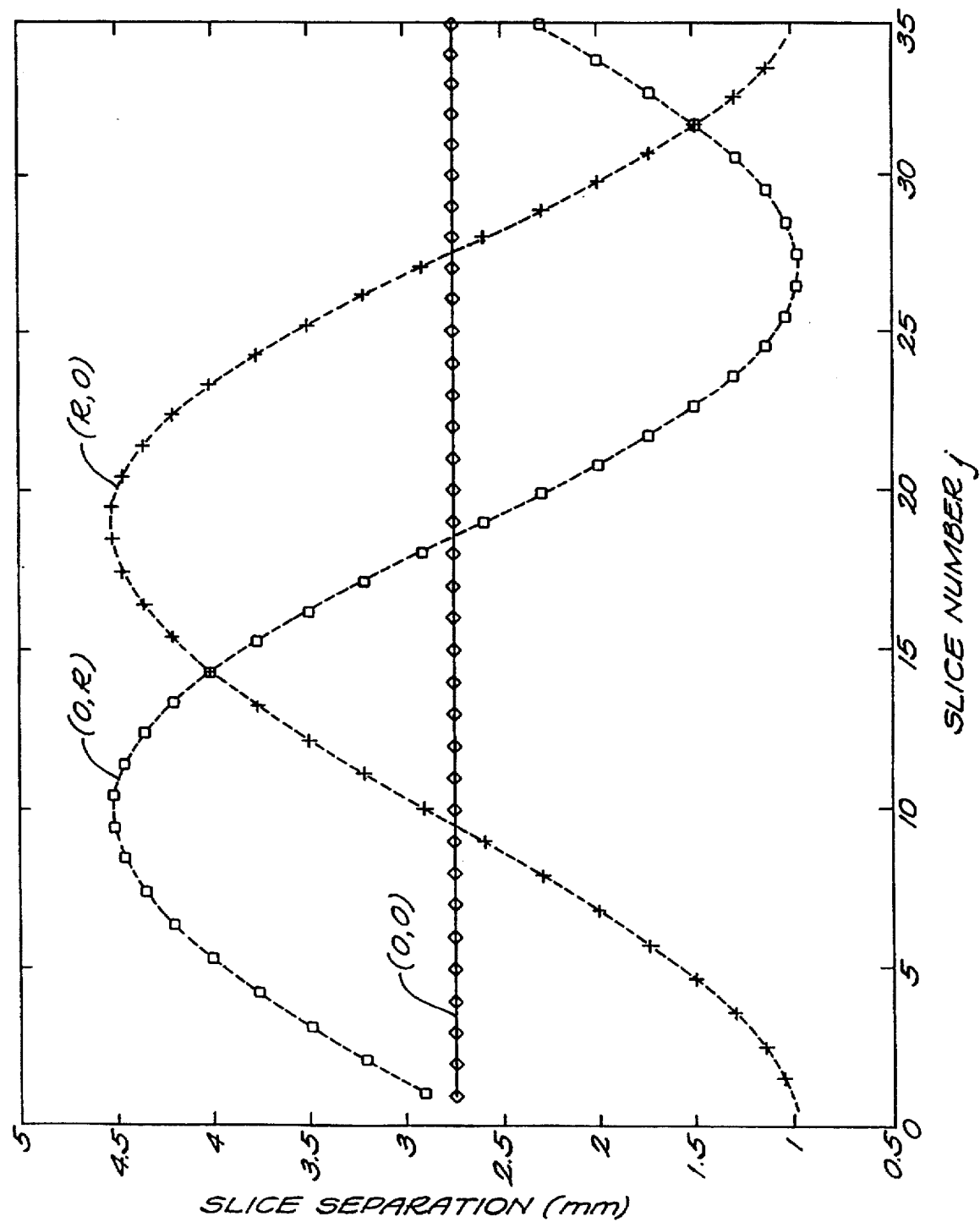
FIG. 12 is a schematic plot which shows slice separation in the z-axis direction in accordance with the present invention.

$\Delta_{zj}$ is sinusoidal, and oscillates about the nominal separation at isocenter which is a constant. FIG. 12 shows the slice separation for pixels located at $(x,y) = (0,0)$, $(R,0)$, and $(0,R)$ where R is the scan radius. Each point on the curve represents a different slice in a series of 36 slices. The slices are separated by 10 views. The curves for $(R,0)$ and $(0,R)$ give the maximum amplitude. Pixels within R will give a smaller amplitude in the slice separation.

Once the fan beam projection data are selected for a given tilted slice, it can be rebinned to parallel beam projection data. One rebinning procedure for continuous variables is disclosed in U.S. Pat. No. Re. 30,947, which is incorporated herein by reference. Here we will describe the rebinning in terms of the discrete data.

Consider rebinning the fan data to 180 degrees of parallel data. As stated previously, the fan views needed to form 180 degrees of parallel views is equal to the number of fan views contained in 180+2$\delta$ degrees of gantry rotation. If an overscan correction is used, more fan views are needed as discussed below. However, the rebinning procedure is the same with or without overscan.

The rebinning can be done in two steps by separating the radial (q-direction) and tangential (v-direction) interpolations. The relation between fan and parallel views is given by $$\beta_p = \beta_f + \gamma_f \quad (25)$$

where $\beta_p$ is the parallel view angle, $\beta_f$ is the fan view angle, and $\gamma_f$ is the fan detector angle. Let $v_p$ be the parallel view index, $(0 \leq v_p < N_p)$, and $v_f$ be the fan view index $(0 \leq v_f < N_h)$. The parallel view angle is given by $$\beta_p[v_p] = v_p \Delta_\beta + \delta \quad (26)$$

where $\Delta_\beta$ is the view angle spacing and $\delta$ is half the fan angle. For each parallel view and fan detector $d_f$, the interpolation point in fan view is calculated, $$v'_f = \frac{1}{\Delta_\beta} (\beta_p[v_p] - \gamma[d_f]) \quad (27)$$

where $\gamma[d_f]$ is the fan detector angle given by $$\gamma[d_f] = \Delta_\gamma (d_f - d_{cf}) \quad (28)$$

and where $d_{cf}$ is the center fan detector. A hybrid parallel projection, $P_h[v_p, d_f]$, is obtained with interpolation in the fan view direction $$P_h[v_p, d_f] = F[v'_f, d_f] \quad (29)$$

The radial interpolation is done as follows. Let t be the location of the desired equi-spaced parallel detectors.

$$t[d_p] = w_{diso}(d_p - d_{cp}) \quad (30)$$

where $w_{diso}$ is the detector channel spacing (in q) at isocenter, $d_p$ is the parallel detector channel number, $(0 \leq d_p < M_p)$, and $d_{cp}$ is the center parallel detector. The number of parallel detectors per view is given by $$M_p = \frac{2R}{w_{diso}} \quad (31)$$

The location of t in the fan detector array is given by $$d'_f[d_p] = \sin^{-1}\left( \frac{t[d_p]}{R} \right) \quad (32)$$

The parallel projection $P[v_p, d_p]$ is obtained by interpolating the hybrid projection data in the $d_f$ $$P[v_p, d_p] = P_h[v_p, d'_f] \quad (33)$$

The combination of the z-interpolation and rebinning consists of interpolation of the cone beam data in all three directions, i.e., $v_f$, d, and r. The z-interpolation can be done first, or it can be inserted into the rebinning procedure.

In stationary CT, parallel views should be symmetric over a range of 180 degrees. That is, a view taken at 0 degrees and a view at 180 degrees should contain the same information in the absence of motion due to symmetry. Object (or patient) motion destroys this symmetry and causes a discontinuity in the projection data for views separated by 180 degrees. This discontinuity results in artifacts in the reconstructed image which lead to the development of correction schemes such as the correction scheme described in U.S. Pat. No. 4,580,219, incorporated herein by reference.

Overscan correction is a method to smooth the discontinuity and decrease motion artifacts. This is accomplished by measuring extra views and weighting them before convolving and backprojecting. The number of extra views is usually small compared to the total number of views contained in $\pi$. Let the number of extra views be $N_{os}$ such that the parallel view data set is given by $0 \leq v_{os} < N_{pos}$, where $N_{pos} = N_p + N_{os}$. The data are first multiplied by weights to give weighted data $$P_w[v_{os}, d_p] = w[v_{os}] P[v_{os}, d_p] \quad (34)$$

where the weight w is given by $$w[v_{os}] = \begin{cases} 3x_1^2 - 2x_1^3 & v_{os} < N_{os} \\ 1 - 3x_2^2 - 2x_2^3 & v_{os} \geq N_p \\ 1 & \text{elsewhere} \end{cases} \quad (35)$$

and where $$x_1 = \frac{v_{os} + 1/2}{N_{os}} \quad (36)$$

$$x_2 = \frac{v_{os} + 1/2 - N_p}{N_{os}} \quad (37)$$

After the weighted data are defined, there are at least two ways to proceed. Let $P_{out}$ be the output parallel projections that are convolved and backprojected. In the first method, the output projections are equal to the weighted projections, namely $$P_{out}[v_{os}, d_p] = P_w[v_{os}, d_p] \quad (38)$$

and the number of views is $N_{pos}$. In the second method, the output projections are given by $$P_{out}[v_p, d_p] = \begin{cases} P_w[v_{os} - N_p, d_p'] + P_w[v_{os}, d_p] & v_{os} \geq N_p \\ P_w[v_{os}, d_p] & \text{elsewhere} \end{cases} \quad (39)$$

where $$d' = M_p - 1 - d \quad (40)$$

and where $0 \leq v_{os} < N_p$. The second method has less output views than the first method. At first it may seem advantageous to backproject less views for computational efficiency. However, in a pipelined architecture the first method may be more efficient. This is because in the second method two views separated by $N_p$ are added together. It may not be possible in a pipeline to save a view in order to add it to another view that is acquired at a later time. Both methods will produce the same final image.

The CT apparatus and method of the invention provide numerous advantages over prior approaches. It provides a three-dimensional scanning approach in the form of helical cone-beam scanning, which is far less time consuming than prior approaches using linear detector arrays. It provides a reconstruction process which results in image quality equivalent to three-dimensional reconstruction algorithms, but does not require three-dimensional reconstruction hardware. The much simpler two-dimensional reconstruction hardware is used.

While this invention has been particularly shown and described with references to preferred embodiments thereof, it will be understood by those skilled in the art that various changes in form and details may be made therein without departing from the spirit and scope of the invention as defined by the following claims.

What is claimed is:

1. A method of reconstructing image data for a region having a longitudinal axis, said method comprising:
   scanning the region with an array of detectors to generate scan data representative of the region;
   defining a plurality of image data slices corresponding to a plurality of positions along the longitudinal axis of the region, successive image data slices being non-parallel with each other; and
   using the scan data, generating image data for the plurality of image slices.

2. The method of claim 1, wherein the region is scanned with a computed tomography (CT) device to generate the scan data.

3. The method of claim 1, wherein the region is scanned with a radiation source which directs radiation through the region onto the array of detectors.

4. The method of claim 3, wherein the radiation source is a cone-beam source.

5. The method of claim 1, wherein successive image data slices are nutated with respect to each other.

6. The method of claim 1, wherein the array of detectors is a two-dimensional array.

7. The method of claim 1, wherein the step of generating image data comprises applying a two-dimensional back projection computation to the scan data.

8. The method of claim 1, wherein the step of generating image data comprises applying a two-dimensional reconstruction computation to the scan data.

9. The method of claim 1, wherein the scan data is generated using a helical scan.

10. The method of claim 1, wherein the scan data is generated using a helical cone-beam scan.

11. The method of claim 10, wherein the step of generating image data comprises applying a two-dimensional back projection computation to the scan data.

12. The method of claim 10, wherein the step of generating image data comprises applying a two-dimensional reconstruction computation to the scan data.

13. The method of claim 1, further comprising rebinning the scan data to parallel-ray scan data.

14. The method of claim 1, further comprising providing overscan correction to the scan data.

15. A method of reconstructing image data for a computed tomography (CT) image of a region, said region having a longitudinal axis and a transverse axis orthogonal to the longitudinal axis, said method comprising:
   scanning the region with a radiation source and an array of detectors to generate scan data representative of the region;
   at each of a plurality of positions along the longitudinal axis of the region, defining image data slice, said image data slice defining a slice plane having a normal axis forming a tilt angle with the longitudinal axis of the region and a rotation angle with the transverse axis of the region such that the normal axes of successive image data slices have the same tilt angle and different rotation angles; and
   using the scan data, generating image data for the plurality of image slices.

16. The method of claim 15, wherein the radiation source is a cone-beam source.

17. The method of claim 15, wherein the array of detectors is a two-dimensional array.

18. The method of claim 15, wherein the step of generating image data comprises applying a two-dimensional back projection computation to the scan data.

19. The method of claim 15, wherein the step of generating image data comprises applying a two-dimensional reconstruction computation to the scan data.

20. The method of claim 15, wherein the scan data is generated using a helical scan.

21. The method of claim 15, wherein the scan data is generated using a helical cone-beam scan.

22. The method of claim 21, wherein the step of computing image data comprises applying a two-dimensional back projection computation to the scan data.

23. The method of claim 21, wherein the step of generating image data comprises applying a two-dimensional reconstruction computation to the scan data.

24. The method of claim 15, further comprising rebinning the scan data to parallel-ray scan data.

25. The method of claim 15, further comprising providing overscan correction to the scan data.

26. The method of claim 15, further comprising, before scanning the region, performing a calibration scan with a tilted opaque disk to determine the tilt angle.

27. The method of claim 26, further comprising computing an area of a projection of the opaque disk on the array of detectors to minimize error in the reconstructed image data.

28. In a computed tomography (CT) system, a method of generating a reconstructed slice of image data comprising:

scanning a region with a radiation source and an array of detectors to generate a plurality of scan data, the region including an axis;

identifying a slice angle between the axis and a slice plane defined by the reconstructed slice such that error in the reconstructed slice image data is minimized; and using the scan data, computing the image data for the reconstructed slice at the slice angle.

29. The method of claim 28, wherein the radiation source is a cone-beam source.

30. The method of claim 28, wherein the array of detectors is a two-dimensional array.

31. The method of claim 28, wherein the image data is computed from the scan data using a two-dimensional reconstruction computation.

32. The method of claim 28, wherein the scan data is generated using a helical scan.

33. The method of claim 28, wherein the scan data is generated using a helical cone-beam scan.

34. The method of claim 28, wherein identifying the slice angle comprises, before scanning the region, performing a calibration scan with a tilted opaque disk.

35. The method of claim 28, further comprising computing an area of a projection of the opaque disk on the array of detectors to minimize error in the reconstructed image data.

36. A system for generating image data for a region having a longitudinal axis, said system comprising:

an array of detectors for scanning the region to generate scan data representative of the region;

processing means for defining a plurality of image data slices at a plurality of positions along the longitudinal axis of the region such that successive image data slices are non-parallel with each other; and generating means for computing image data for the plurality of image slices.

37. The system of claim 36, wherein the system is a computed tomography (CT) system.

38. The system of claim 36, further comprising a radiation source for directing radiation through the region and onto the array of detectors to scan the region.

39. The system of claim 38, wherein the radiation source is a cone-beam source.

40. The system of claim 36, wherein the array of detectors is a two-dimensional array.

41. The system of claim 36, wherein the generating means comprises two-dimensional back projection means for generating the image data.

42. The system of claim 36, wherein the generating means comprises two-dimensional reconstruction means for generating the image data.

43. The system of claim 36, further comprising two-dimensional back projection hardware for generating the image data.

44. The system of claim 36, wherein the array of detectors is adapted to perform a helical scan of the region.

45. The system of claim 36, wherein the array of detectors is adapted to perform a helical cone-beam scan of the region.

46. The system of claim 36, further comprising means for rebinning the scan data to parallel-ray scan data.

47. The system of claim 36, further comprising means for providing overscan correction to the scan data.

48. The system of claim 36, further comprising means for performing a calibration scan with a titled opaque disk before scanning the region.

49. The system of claim 48, further comprising means for computing an area of a projection of the opaque disk on the array of detectors to minimize error in the reconstructed image data.

* * * * *